US006840913B2

(12) United States Patent
Mansy et al.

(10) Patent No.: US 6,840,913 B2
(45) Date of Patent: Jan. 11, 2005

(54) ACOUSTIC DETECTION OF GASTRIC MOTILITY DYSFUNCTION

(75) Inventors: Hansen A. Mansy, Justice, IL (US); Richard H. Sandler, Evanston, IL (US)

(73) Assignee: Biomedical Acoustic Research Corp., Evanston, IL (US)

(*) Notice: Subject to any disclaimer, the term of this patent is extended or adjusted under 35 U.S.C. 154(b) by 270 days.

(21) Appl. No.: 10/093,906

(22) Filed: Mar. 8, 2002

(65) Prior Publication Data

US 2002/0156398 A1 Oct. 24, 2002

Related U.S. Application Data

(60) Provisional application No. 60/274,908, filed on Mar. 9, 2001.

(51) Int. Cl.[7] ............................. A61B 7/00; A61B 5/103
(52) U.S. Cl. ...................................... 600/586; 600/593
(58) Field of Search ................................ 600/586, 593; 128/920, 923

(56) References Cited

U.S. PATENT DOCUMENTS

| | | |
|---|---|---|
| 4,823,808 A | 4/1989 | Clegg et al. |
| 4,991,581 A | 2/1991 | Andries |
| 5,010,889 A | 4/1991 | Bredesen et al. |
| 5,183,457 A | 2/1993 | Gatts et al. |
| 5,853,005 A | 12/1998 | Scanlon |
| 6,056,703 A | 5/2000 | Sandler et al. |
| 6,287,266 B1 | 9/2001 | Sandler et al. |

FOREIGN PATENT DOCUMENTS

| | | |
|---|---|---|
| DE | 3830412 | 8/1990 |
| WO | WO 97/36543 | 10/1997 |
| WO | WO 99/49778 | 10/1999 |

OTHER PUBLICATIONS

Mansy et al., "Detection and Analysis of Gastrointestinal Sounds in Normal and Small Bowel Obstructed Rats," Medical and Biological Engineering and Computing, vol. 38, No. 1, Jan. 2000, pp. 42–48.

Tomomasa et al., "Gastrointestinal Sounds and Migrating Motor Complex in Fasted Humans," American Journal of Gastroenterology, vol. 94, No. 2, Feb. 1999, pp. 374–381.

Mansy H., et al.; "Rapid Detection of Delayed Gastric Emptying;" NIH Research Grant Application, Granted Sep. 28, 1999.

Sugrue M. et al; "Computerized Ponoenterography: The Clinical Investigation of a New System;" J Clin Gastroenterol 1994; 18(2): pp. 139–144.

Dalle D. et al; "Computer Analysis of Bowel Sounds;" 1974: pp. 247–256.

*Primary Examiner*—Eric F. Winakur
(74) *Attorney, Agent, or Firm*—Hanley, Flight & Zimmerman, LLC (57) ABSTRACT

A system and method for detecting a gastric motility dysfunction acquires acoustic event information associated with a body and compares the acquired acoustic event information to information associated with a healthy condition. The system and method then identifies the gastric motility dysfunction based on the comparison of the acquired acoustic event information to the information associated with the healthy condition.

35 Claims, 5 Drawing Sheets

| Region | Arrival Order |
|---|---|
| I | 31,33,32 |
| II | 31,32,33 |
| III | 32,31,33 |
| IV | 32,33,31 |
| V | 33,32,31 |
| VI | 33,31,32 |

ACOUSTIC DETECTION OF GASTRIC MOTILITY DYSFUNCTION

RELATED APPLICATIONS

This application claims the benefit of the filing date of U.S. Provisional Patent Application No. 60/274,908, entitled "Acoustic Detection of Gastric Motility Dysfunction," filed on Mar. 9, 2001.

BACKGROUND OF THE INVENTION

1. Technical Field

The present invention relates generally to the non-invasive diagnosis of conditions within a human or animal body and, more particularly, the invention relates to using gastric sounds to diagnose gastric motility dysfunction.

2. Description of Related Technology

One form of gastric motility dysfunction is delayed gastric emptying (DGE) which refers to an abnormal slowing of the emptying of gastric contents into the duodenum. DGE may result from structural lesions such as, for example, an ulcer, a neoplasm, an obstruction, etc. or may result from a motility disorder, which is commonly referred to as gastroparesis. Gastroparesis may be idiopathic or may result from diabetic gastropathy, scleroderma or other disorders. If untreated, gastroparesis may cause debilitation from nausea, vomiting, bloating, abdominal pain, weight loss and malnutrition. Other complications of gastroparesis such as malabsorption of medicines and glucose regulation difficulties in diabetic patients have been observed.

Symptoms of DGE vary and are often collectively referred to as dyspepsia. Symptoms of DGE include abdominal discomfort or pain, early satiety, distention, bloating, nausea, vomiting, belching and epigastric or retrosternal burning or pyrosis. Although the precise incidence of DGE is uncertain, the incidence of DGE may be estimated from the incidence of dyspeptic symptoms and from studies suggesting how often DGE is etiologic for dyspepsia. About 25% of adults experience dyspepsia on a regular basis and as many as 50% of gastrointestinal clinic patients suffer from dyspeptic symptoms. Although some patients with dyspepsia do not have DGE, DGE may underlie or contribute to dyspeptic symptoms in over 30% of these patients. In certain disease states, the incidence of DGE may be increased, especially long standing insulin-dependent diabetics for which the incidence of DGE typically ranges between about 27% and 58%.

The current techniques for diagnosing DGE include barium radiography, gastric and antroduodenal manometry, dilution methods, cutaneous electrogastrography and radionuclide gastric emptying scintigraphy. While gastric emptying scintigraphy is the most accurate technique for diagnosing DGE, this technique is expensive, involves radiation, is time consuming and is not readily portable. Many other known techniques for diagnosing DGE are of limited utility because of their low accuracy.

SUMMARY OF THE INVENTION

A technique for using gastric sounds to diagnose a gastric motility dysfunction such as, for example, DGE in humans and animals is described herein. Generally speaking, the diagnostic technique detects acoustic events at or near the surface of a patient's abdomen and processes electrical signals corresponding to these acoustic events to determine whether the patient is afflicted with a gastric motility dysfunction. In particular, the diagnostic technique may determine the locations of the individual acoustic events and may also determine the temporal and/or spectral characteristics of the acoustic events. The technique may use the location information to selectively process those acoustic events that are gastric sound events that may be indicative of a gastric motility dysfunction. Alternatively or additionally the technique may compare the temporal and/or spectral information of the acoustic events to the temporal and/or spectral characteristics of gastric sounds generated within a normal or healthy patient. The technique may, based on the comparison, provide a diagnostic output to a user.

In accordance with one aspect of the invention, a system and method of detecting a gastric motility dysfunction may acquire a plurality of signals associated with sounds emanating from an abdominal region of a body and may calculate an envelope of the plurality of signals. The system and method may detect a plurality of acoustic events based on the envelope of the plurality of signals and may calculate a characteristic of the plurality of acoustic events. Additionally, the system and method may determine whether the characteristic of the plurality of acoustic events corresponds to the gastric motility dysfunction.

In accordance with another aspect of the invention, a system for detecting a gastric motility dysfunction may include a computer readable medium, and software stored on the computer readable medium and adapted to be executed by a processor. When executed by the processor, the software may cause the processor to acquire a plurality of signals associated with sounds emanating from an abdominal region of a body, calculate an envelope of the plurality of signals, detect a plurality of acoustic events based on the envelope of the plurality of signals, calculate a characteristic of the plurality of acoustic events and determine whether the characteristic of the plurality of acoustic events corresponds to the gastric motility dysfunction.

In accordance with yet another aspect of the invention, a method of detecting a gastric motility dysfunction may acquire acoustic event information associated with a body and may compare the acquired acoustic event information to information associated with a healthy condition. Additionally, the method may identify the gastric motility dysfunction based on the comparison of the acquired acoustic event information to the information associated with the healthy condition.

DETAILED DESCRIPTION OF THE PREFERRED EMBODIMENTS

While a DGE diagnostic technique is described herein in connection with a human patient, it should be understood that the diagnostic technique described herein may be more generally applied to detect and diagnose other types of gastric motility dysfunction and/or to other animals to achieve the same or similar results. Further, although the diagnostic technique is described by way of example as being implemented using digital signal processing techniques, analog signal processing techniques may be used instead. Additionally, it should be recognized that the diagnostic technique described herein may be used within a relatively stationary unit, may be used within a portable ambulatory unit and/or may be used within a telemedicine application (i.e., a system having a data acquisition unit in communication with a remote host that processes collected data to generate diagnostic results). In any event, before discussing the DGE diagnostic technique in greater detail, a brief discussion of how gastric sounds are generated and how these gastric sounds are related to DGE is provided below.

A DGE condition is typically accompanied by a reduction in the net flow of gastric chyme through the stomach exit or pylorus. Such a flow reduction is commonly referred to as a transpyloric flow reduction and may be due to reduced driving force (i.e., coordinated motility of adequate strength) or increased resistance to flow. These gastric flow reduction mechanisms are fundamentally different from one another and result in different gastric sound characteristics. More specifically, the qualities of these gastric sounds such as the duration, strength and relative timing of the transpyloric flow may be indicative of a DGE condition.

Generally speaking, gastric sound events are intermittent aperiodic (i.e., they may reoccur but at varying intervals) bursts of acoustic activity. Gastric sounds are a subclass of gastrointestinal sounds and typically emanate from the stomach, pylorus and proximal duodenal regions. While the exact mechanisms of gastric sound generation are not well known, it appears that the turbulent flow generated by a heterogeneous mixture of chyme and gas bubbles being forced by contracting gastric muscles across the narrow pylorus may be the principal mechanism by which gastric sounds are generated. Gastric sound events typically have a wide range of characteristics, change with motility phases, originate from all abdominal regions and are attenuated before reaching the surface of a patient where they may be detected by a device such as an electronic stethoscope, microphone, etc.

The peristaltic activity of the stomach of a healthy patient (i.e., a patient that is not afflicted with DGE) typically generates about three gastric sound events per minute. Additionally, gastric sound events may be distinguished from other abdominal acoustic events. For example, gastric sounds are typically wideband transient acoustic events that emanate as bursts from the epigastric region of the abdomen. Further, these gastric sound events typically have durations of 5–800 milliseconds and a spectral content including frequencies between about 50 Hertz (Hz) and 2 kilohertz (kHz).

The diagnostic technique described herein detects sounds or vibrations at or near the surface of a patient's abdominal wall, converts these detected sounds or vibrations into electrical signals and then analyzes the electrical signals to determine whether the patient is afflicted with a gastric motility dysfunction such as DGE. The analysis of the electrical signals may determine the origin or locus of the detected gastric sounds to thereby determine whether the gastric sounds are likely to have been caused by a gastric motility dysfunction. Additionally, the analysis may compare the temporal and/or frequency domain characteristics of the electrical signals acquired from the patient being examined to the characteristics associated with a typical healthy patient to determine whether the patient being examined is afflicted with a particular gastric motility dysfunction.

Figure 1:
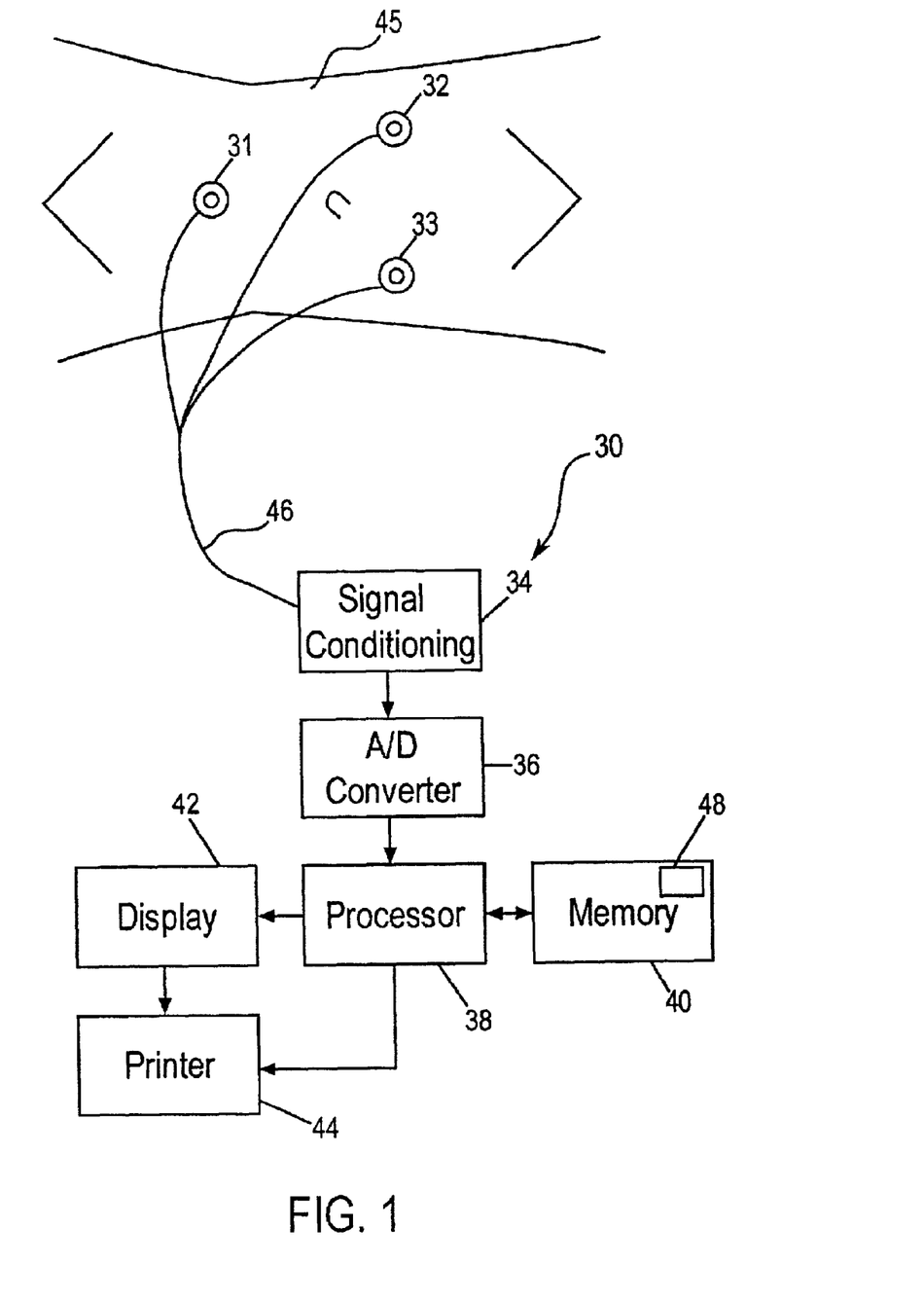
FIG. 1 is an exemplary schematic block diagram of a system that uses gastric sounds to diagnose DGE in a human patient.

FIG. 1 is an exemplary schematic block diagram of system 30 that uses gastric sounds to diagnose a DGE condition in a human patient. As shown in FIG. 1, the system 30 includes sensors 31–33, a signal conditioning block 34, an analog-to-digital (A/D) converter 36, a processor 38, a memory 40, a display 42 and a printer 44.

The sensors 31–33 may be contact or non-contact transducers that detect vibrations or sounds at or near the skin surface and convert these vibrations or sounds into electrical signals. Other sensors may include internal sensors such as intra-esophageal and intra-gastric sensors that are introduced into the patient using a nasal-gastric tube or the like. By way of example only, the sensors 31–33 may be electronic stethoscopes, accelerometers, contact microphones, non-contact vibration sensors such as capacitive or optical sensors, or any other suitable type of sensors. In some applications, an electret condenser air-coupled electronic stethoscope may be selected for its sensitivity over a wide bandwidth, low cost, durability and ease of use. In any event, the sensors 31–33 are preferably, but not necessarily, selected to have an acoustic impedance that matches the impedance of the skin surface to provide optimal acoustic coupling to the skin surface. Still further, due to background noise and the relatively low amplitude of the vibrations or sounds which are generated at or near the skin surface by gastric sounds, the sensors 31–33 are also preferably, but not necessarily, selected to provide a high signal-to-noise ratio, high sensitivity and good ambient noise shrouding capability.

While three sensors are shown in FIG. 1, additional or fewer sensors may be used to detect gastric sounds at multiple locations on the patient's abdomen 45, or any other locations on the patient's body that are of interest and which may be useful in detecting a gastric motility dysfunction such as, for example, DGE. For example, a single sensor may be strategically located on the patient's body and/or may be moved sequentially to different key locations on the patient's body to detect gastric sounds.

The sensors 31–33 send low level (i.e., low power) electrical signals via wires 46, or any other suitable media such as wireless radio frequency, infrared, etc., to the signal conditioning block 34. The signal conditioning block 34 may include amplifiers, filters, transient protection and other circuitry that amplifies the signals sent by the sensors 31–33, that attenuates noise signals, and that reduces the effects of aliasing. In particular, the signal conditioning block 34 may include a low-pass filter having a cutoff frequency of about 2000 Hz. Alternatively or additionally, a high-pass filter may be incorporated within the signal conditioning block 34. This high-pass filter may, for example, have a cutoff frequency of about 75 Hz so that undesirable noise and sounds, such as muscle noise, breathing sounds, cardiac sounds, non-gastric gastrointestinal sounds or any other undesirable sounds or noise are substantially attenuated or eliminated before the signals sent by the sensors 31–33 are processed further. The spectral energy of the most potentially corrupting non-gastrointestinal sounds are in a frequency band of 20 Hz to 250 Hz. However, the amplitude of these corrupting sounds may be significantly reduced for adult patients by optimally positioning the sensors 31–33.

The A/D converter 36 receives the signal conditioned analog output signals from the signal conditioning block 34 and converts the received analog signal values into digital information, which can be processed by the processor 38, as described in greater detail below. The processor 38 may be integral to a personal computer, may be integral to a microcontroller integrated circuit chip, may be implemented using a custom integrated circuit chip, or may be implemented using any other electronic device suitable for carrying out the methods described herein.

The memory 40 is communicatively coupled to the processor 38 and may include software 48 that, when executed by the processor 38, causes the processor 38 to carry out the methods described herein. It should be recognized that the processor 38 and the memory 40 may be integral to a personal computer or, alternatively, may be implemented using one or more custom, semi-custom or commonly available integrated circuits. Further, it should be recognized that the software 48 may include one or more software routines that are implemented using any of a variety of programming techniques and languages without departing from the scope and the spirit of the invention.

The display 42 may be any conventional video monitor or any other suitable display that communicates with the processor 38 and which can display graphic and/or textual information relating to the gastric sounds detected by one or more of the sensors 31–33. Thus, the information generated on the display 42 may facilitate medical personnel in diagnosing whether a patient is afflicted with DGE. For example, the display 42 may graphically represent the temporal and/or spectral characteristics of the gastric sounds detected at a particular location of the patient's body, which may be associated, for example, with the stomach, small intestine, or any other portion of the patient's gastrointestinal system. The displayed temporal and/or spectral characteristics may then be used to determine if the patient being examined is afflicted with DGE by, for example, comparing the acquired temporal and/or spectral characteristics to reference temporal and/or spectral characteristics associated with normal or acceptable gastric sounds. In addition, the signals acquired from the sensors 31–33 may be further used to determine the precise location, origin or locus of the detected gastric sounds. Alternatively or additionally, the display 42 may include a plurality of indicators (such as, for example, color coded lights and/or distinct sounds) that may be used to indicate a diagnostic result.

The printer 44 may be used to generate hard copies of textual and/or graphical information, including the information which is displayed on the display 42. For example, numerical and graphical temporal and/or spectral information may be printed to facilitate off-line analysis of test results by medical personnel and/or to facilitate the generation of permanent test results documentation for records, reports, etc.

Figure 2:
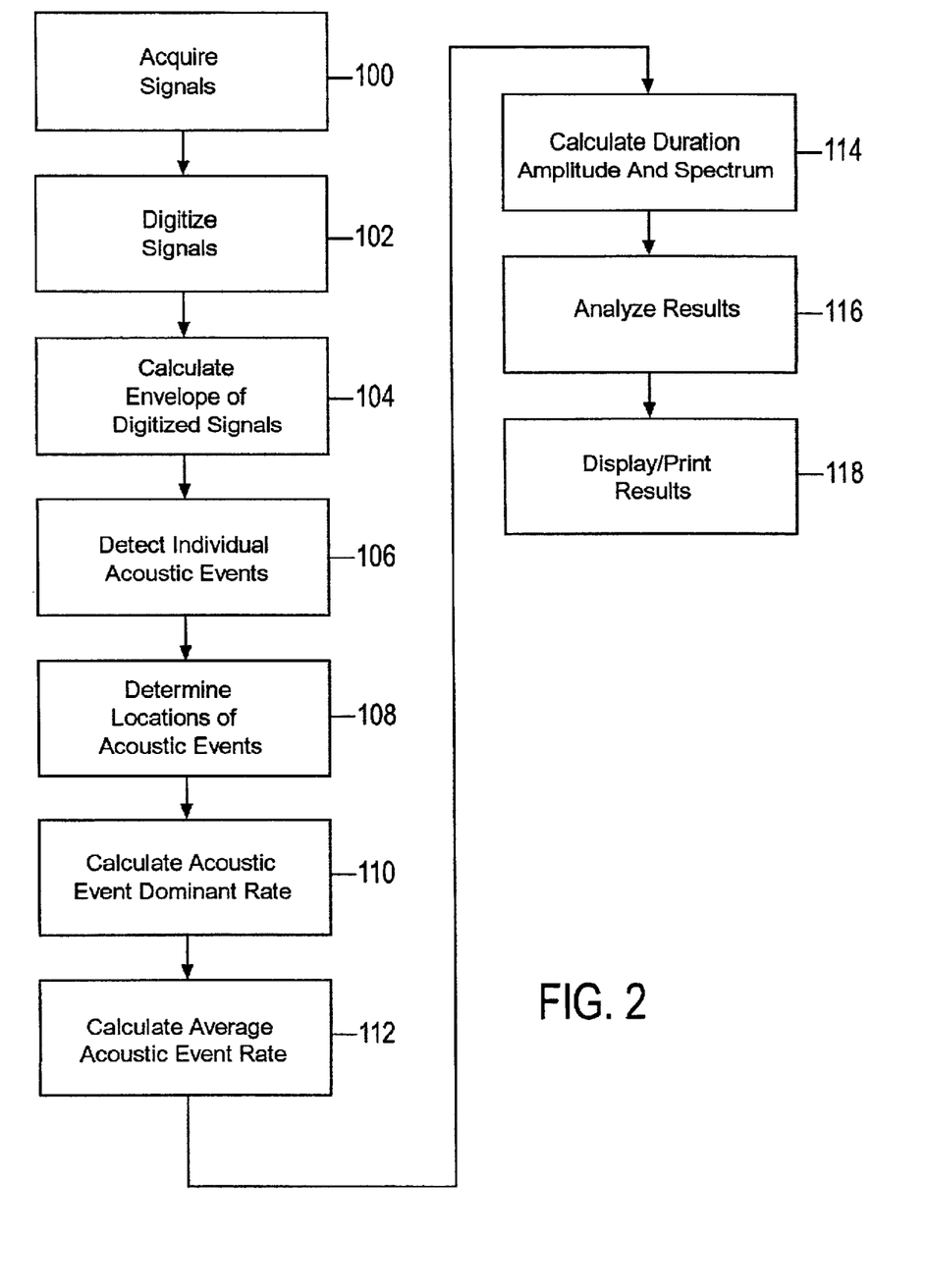
FIG. 2 is an exemplary flow diagram representing one method by which the system shown in FIG. 1 may detect and diagnose a DGE condition.

FIG. 2 is an exemplary flow diagram representing one method by which the system shown in FIG. 1 may detect and diagnose DGE. Block 100 acquires analog electrical signals from one or more of the sensors 31–33 (FIG. 1). Block 100 may use the signal conditioning block 34 (FIG. 1) to filter noise, amplify the signals, etc. as discussed above before the signals are processed by block 102. Further, block 100 may acquire signals from one or more of the sensors 31–33 for a period of time sufficient to capture a plurality of gastric sound events. For example, block 100 may acquire signals from one or more of the sensors 31–33 for a period of time equal to the time typically required to capture ten gastric sound events. Of course, block 100 may acquire sounds or vibrations for a period of time that corresponds to more or fewer gastric sound events without departing from the scope of the invention.

The sensors 31–33 may be arranged in any desired manner to facilitate the acquisition of gastric sounds and to facilitate the detection and diagnosis of DGE. In particular, one of the sensors 31–33 (e.g., the sensor 31) may be located directly over the upper central portion of the patient's abdomen 45 (e.g., just below the xyphoid) and the sensors 32 and 33 may be located over opposing sides of the lower portion of the abdomen 45 (e.g., the left and right quadrants) as shown in FIG. 1. Of course, the sensors 31–33 may be moved to locations other than those specifically depicted in FIG. 1 without departing from the scope and the spirit of the invention. For example, the sensor 31 may be located on a traverse line two-thirds of the distance between the umbilicus and xyphoid to the right of the midline, sensor 32 may be located over the left costal margin and sensor 33 may be located at the midline at one-half of the distance between the umbilicus and symphosis pubis.

Block 102 converts the analog signals acquired by block 100 into digital data using, for example, the A/D converter 36 shown in FIG. 1. Typically, but not necessarily, the analog data is digitized at a sampling rate of 8192 Hz. However, other sampling rates may be used to achieve any desired frequency resolution.

Block 104 calculates the envelopes of the digitized signals associated with each of the sensors 31–33. Block 104 may use a Hilbert transform or any other suitable calculation technique to calculate the signal envelopes. Block 106 uses amplitude thresholding to detect individual acoustic events (some of which may be gastric sound events) within the signal envelopes. Block 106 may use a predetermined amplitude value to discriminate between background noise and acoustic events. In particular, block 106 may determine that an individual acoustic event (e.g., a gastric sound event) has occurred when the amplitude of an envelope exceeds the predetermined amplitude value. Additionally or alternatively, Blocks 104 and 106 may use wavelet analysis or any other temporal or spectral feature analysis to detect individual acoustic events.

Block 108 assigns detected acoustic events to particular abdominal regions using amplitude and/or signal transit time-based analysis techniques. For example, referring to FIG. 3, in the case where three sensors (e.g., the sensors 31–33) are used, the patient's abdomen 45 may be subdivided into six regions defined by three boundary lines. Each of the boundary lines extends through a respective one of the sensors 31–33 and the midpoint between the other two sensors. Additionally, the outermost peripheries of the six regions may be further defined by the outer dimensions of the patient's abdomen 45.

Figure 4:
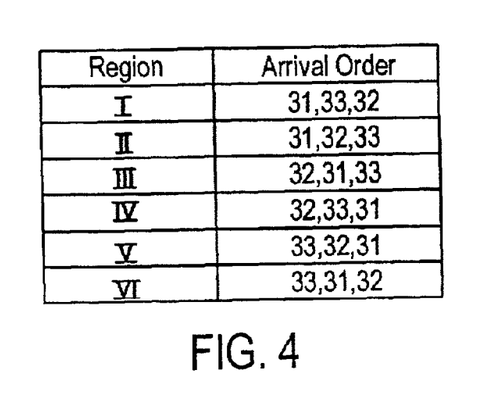
FIG. 4 is an exemplary table depicting one manner in which the arrival order of the signals received by the acoustic sensors shown in FIG. 1 may be used to determine from which of the regions shown in FIG. 3 an acoustic event originated.

Block 108 may then determine the order in which each of the acoustic events identified by block 106 arrived at each of the sensors 31–33. In other words, each acoustic event may be independently detected by each of the sensors 31–33 but at different times owing to the fact that the locus or origin of the acoustic event may be different distances from each of the sensors 31–33. In any event, block 108 may use a table stored in the memory 40 (FIG. 1) such as that shown in FIG. 4 to map or assign acoustic event arrival orders to abdominal regions. By way of example, if block 108 determines that an acoustic event was first received by sensor 31 then by sensor 33 and last by sensor 32, block 108 will assign that acoustic event to region one.

Figure 3:
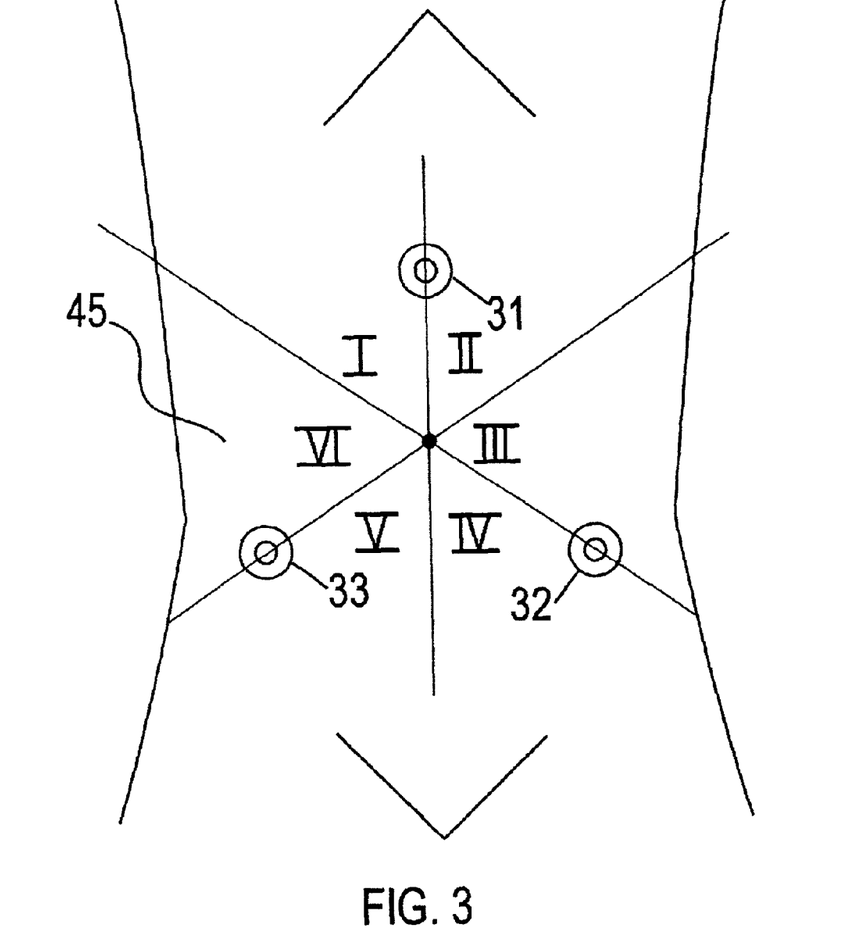
FIG. 3 is an exemplary diagram depicting one manner in which a patient's abdominal region may be subdivided into a plurality of regions for use with the method shown in FIG. 2.

Alternatively, block 108 may use maximum signal amplitudes instead of signal arrival order to assign acoustic events to the abdominal regions shown in FIG. 3. Because sounds are attenuated as they travel through a patient's body, each of the sensors 31–33 may detect a different maximum signal amplitude for a particular acoustic event. Thus, those sensors detecting a larger amplitude are nearer (both in time and distance) to the locus of the acoustic event. Thus, arranging signals in order of decreasing maximum amplitude results in the same sequence as when signals are arranged in order of earliest to latest arrival time. As a result, block 108 may also use the table shown in FIG. 4 to assign acoustic events to the abdominal regions shown in FIG. 3 based on signal amplitudes. By way of example, if the sensor 31 detects the largest amplitude, the sensor 33 detects the next largest amplitude, and the sensor 32 detects the smallest amplitude, then block 108 assigns the acoustic event to region one.

Yet another alternative approach that may be used by block 108 to determine the abdominal locations of acoustic events uses relative time delay values to precisely determine the locus of the acoustic events. For example, block 108 may use the phase of the cross-correlation between the signals received by each of the sensors 31–33 to determine relative time delay values for each sensor pair. The time delay between each sensor pair corresponds to a hyperbolic curve that describes possible locations for the locus of the acoustic event. In the case of a three sensor array, such as that used by the system shown in FIG. 1, two such hyperbolic equations may be solved simultaneously to yield a precise locus for each acoustic event. Practically speaking, the computational efficiency of this technique may be improved by solving these hyperbolic functions for a range of time delay values (which in the above example would require two time delay values) and storing the results in a multi-dimensional table within the memory 40. In this manner, block 108 could retrieve calculation results directly from the table stored in the memory 40 based on the measured time delay values and, thus, would not have to solve the hyperbolic functions during a diagnostic procedure.

Still another alternative approach that may be used by block 108 to determine the locations of the acoustic events identified by block 106 uses a beam forming technique. With this approach, an acoustic event is recomposed by time shifting the signals received by each of the sensors 31–33 in connection with that acoustic event to temporally align the signals with respect to a particular location within the patient's abdominal region. In other words, each of the signals received by the sensors 31–33 are time shifted by an amount equal to the time required for a sound wave to travel from that particular location to a respective sensor. The actual source of the acoustic event may then be determined by varying the particular location to find the location at which the recomposed acoustic event has a maximum amplitude. The use of a beam forming approach by block 108 to determine the locus of acoustic events may be advantageous because such an approach results in the destructive summation of indirect or reflected signals, thereby increasing the accuracy with which the locus of an acoustic event can be determined. Additionally, the contribution of these indirect or reflected signals to the summation may be shifted to different frequencies and, thus, may be further attenuated using, for example, one or more band-pass filters.

Block 110 calculates the dominant rate of the acoustic events detected by block 106. Block 110 may, for example, calculate acoustic event rates by dividing one by the time period between each of two consecutive acoustic events. The resulting acoustic event rates may then be analyzed by block 110 to determine the rate which most frequently occurs or which is most probable. The most frequent or probable rate may then be considered the dominant rate of the detected acoustic events.

Block 112 determines the average acoustic event rate by summing the total number of acoustic events identified by block 106 and dividing that sum by the total acquisition period. Block 114 calculates the duration, amplitude and spectral content of each of the acoustic events identified by block 106. It should be recognized that while block 114 may calculate the duration and amplitude of the individual acoustic events, the results of block 104 (which provides envelopes of the acoustic events) and the results of block 106 (which determines event durations via the thresholding process described above) may be used instead. Block 114 may also calculate the average amplitude and maximum amplitude for each acoustic event. The maximum and average amplitudes may be used to characterize or determine the nature of particular acoustic events. Block 114 may further calculate the spectral content of each acoustic event using any suitable technique such as, for example, a fast Fourier transform (FFT). Of course, other data analysis techniques or algorithms such as autoregressive modeling, wavelet decomposition or zero crossing rate may be used instead of or in addition to a FFT to transform the digitized signal information into frequency domain or spectral information.

If desired, blocks 110–114 may use the results of block 108 to eliminate acoustic events that did not originate within abdominal regions associated with gastric sounds and/or a DGE condition. In this manner, blocks 110–114 may more precisely calculate the dominant acoustic event rate, the average acoustic event rate and the spectral content of acoustic events for those gastric sounds which are of particular interest (i.e., those which may be indicative of whether or not a DGE condition is present).

Block 116 may use the results of blocks 104–114 to determine whether the patient being examined is afflicted with a DGE condition. For example, block 116 may compare the dominant and/or average acoustic event rates calculated by blocks 110 and 112, respectively, to predetermined thresholds associated with a normal patient, who is not afflicted with DGE. If block 116 determines that one or both the dominant and average acoustic event rates are sufficiently different from the predetermined thresholds, then block 116 may generate a diagnosis indicating that the presence of a DGE condition is likely. Alternatively or additionally, block 116 may analyze the spectral content of the events calculated by block 114 to determine whether a DGE condition is present. If block 116 determines that the spectral content of the acoustic sound events includes relatively few or completely lacks long duration acoustic events, block 116 may generate a diagnosis indicating that the presence of DGE is likely. Alternatively or additionally, block 116 may use the acoustic event location information generated by block 108 to determine whether the locus of the acoustic sound events is moving in a manner consistent with a DGE condition. If block 116 determines that the locus of the acoustic sound events is moving along the long axis of the patient's stomach and pyloric region in an abnormal fashion, block 116 may generate a diagnosis indicating that the presence of a gastric motility dysfunction is likely. Still further, block 116 may combine the results of one or more of the above-described diagnostic tests to generate a composite diagnosis. By way of example only, block 116 may use neural network techniques, which are well known, to produce a composite diagnosis based on one or more of the calculated parameters. Block 118 may be used to display and/or print graphical or textual information provided by any of blocks 104–116 described above.

Figure 5:
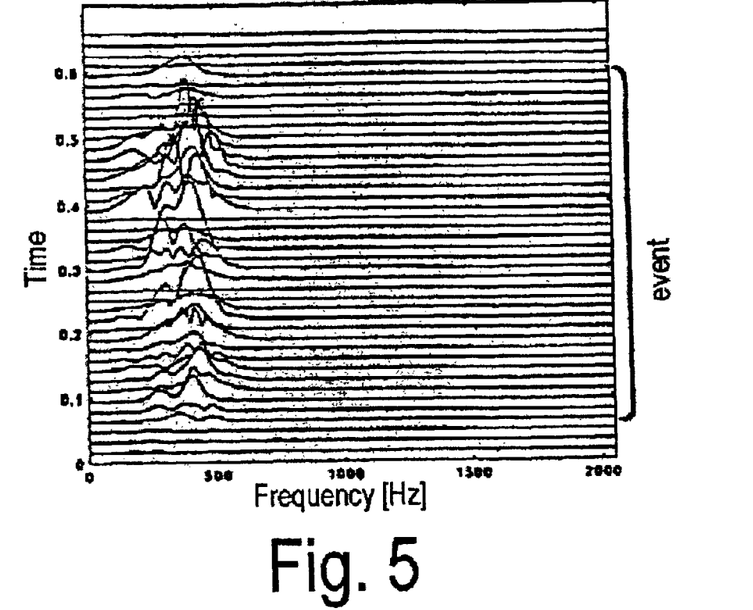
FIG. 5 is a graphical representation of the time dependent spectral characteristics of a gastric sound event within a normal human patient.
Figure 6:
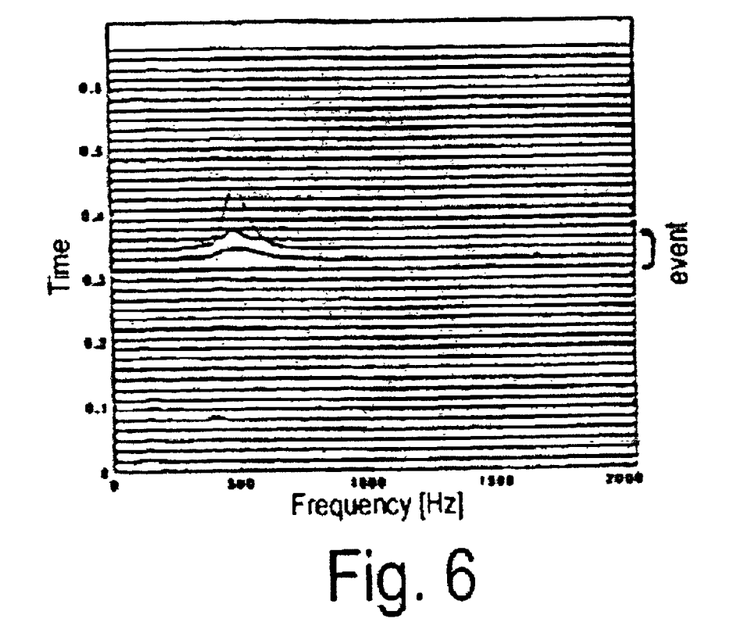
FIG. 6 is a graphical representation of the time dependent spectral characteristics of a gastric sound event within a human patient having a DGE condition.

FIG. 5 is a graphical representation of the time dependent spectral characteristics of a gastric sound event within a normal human patient and FIG. 6 is a graphical representation of the time dependent spectral characteristics of a gastric sound event within a human patient having a DGE condition. As can be seen from FIGS. 5 and 6, a DGE condition typically results in a substantial reduction in the duration of gastric sound events.

Figure 7:
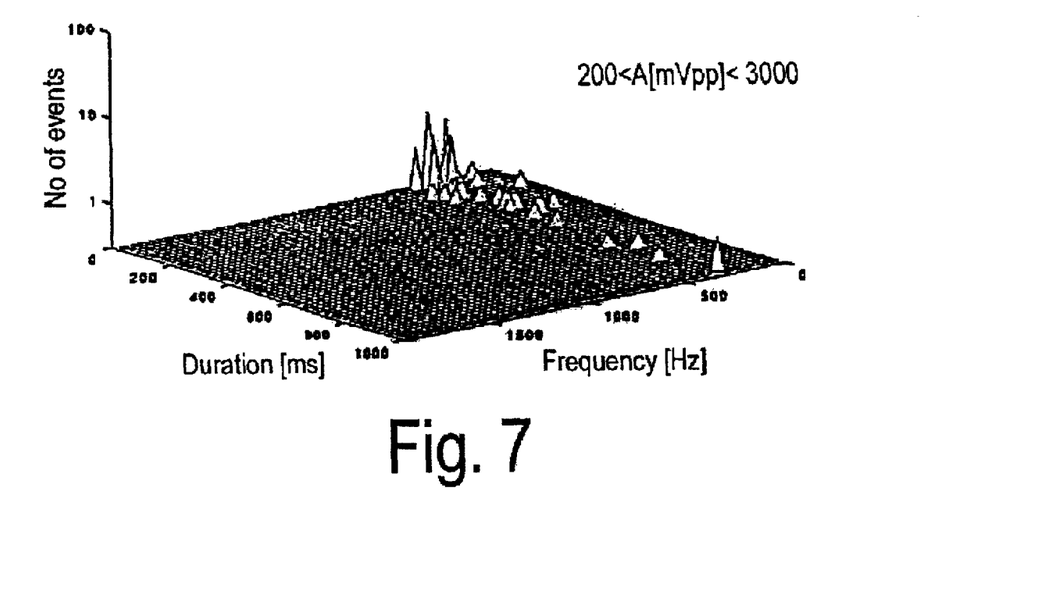
FIG. 7 is an exemplary graphical representation of the distribution of the spectral content and durations of a plurality of gastric sound events generated within the abdominal region of a normal human patient.
Figure 8:
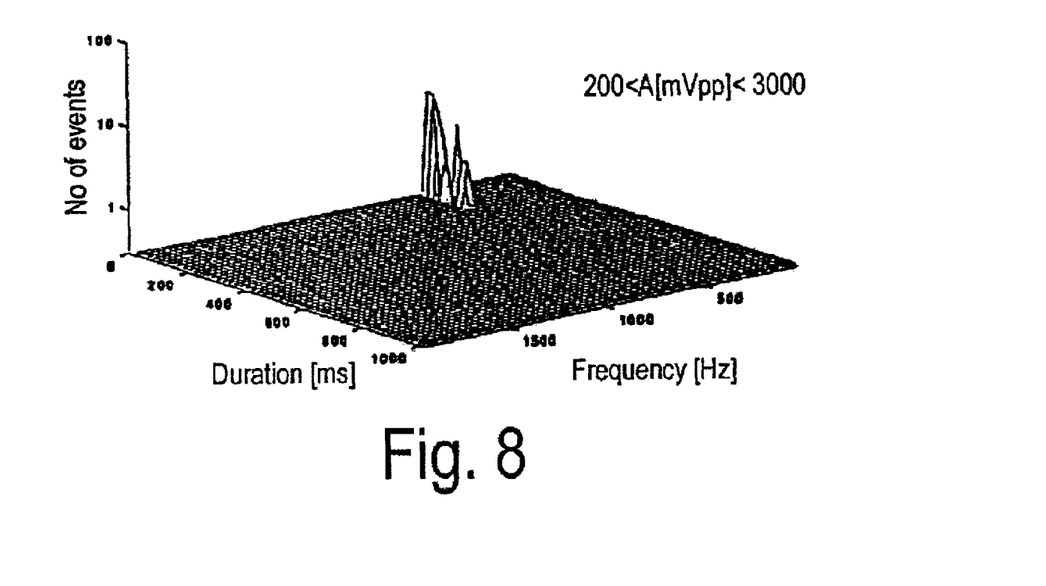
FIG. 8 is an exemplary graphical representation of the distribution of the spectral content and durations of a plurality of gastric sound events generated within the abdominal region of a human patient having a DGE condition.

FIG. 7 is an exemplary graphical representation of the distribution of the spectral content and durations for a plurality of gastric sound events within a normal human patient and FIG. 8 is an exemplary graphical representation of the distribution of the spectral content and durations for a plurality of gastric sound events within a human patient having a DGE condition. As shown in FIGS. 7 and 8, a DGE condition may be characterized by an absence of long duration gastric sound events (i.e., events having durations greater than about 200 milliseconds) such as those which may occur in connection with propulsive sounds.

The use of a standard meal may increase the accuracy of the DGE diagnostic technique described herein because meal composition and calorie content may affect gastric emptying. Osmolarity, pH, fat composition (especially medium chain triglycerides), carbohydrate load and protein have all been reported to trigger small bowel receptors, thereby resulting in slowed gastric emptying. The normal emptying of solids and liquids is different from that found in a patient having a DGE condition. In normal emptying of solids, an initial lag phase, during which little or no solid is emptied, is followed by a prolonged phase of constant emptying and a subsequent slower phase. On the other hand, emptying of neutral and calorically inert liquids is monoexponential without the initial lag phase. When a combined solid-liquid meal is given, liquids empty faster than solids but slower than if only liquids are used. For the diagnostic technique described herein, the emptying of both solids and inert liquids is assessed. However, the use of other standard meals, including those with non-inert liquids, also provides additional useful information. Furthermore, adding air or gas to the gastric contents (e.g., via ingestion of carbonated beverages or the like) may act as an enhancing agent that increases the amplitude of gastric sounds, thereby improving signal-to-noise ratio, which may further improve the diagnostic capability of the diagnostic technique described herein.

While the diagnostic technique has been described above in connection with diagnosing DGE, it is important to recognize that the distribution of the acoustic event rate may, in general, be used to distinguish normal or healthy patients from those having a gastric motility dysfunction. For example, healthy patients are more likely to display a gastric emptying sound rate of about three acoustic events per minute. On the other hand, abnormal patients may display many different gastric sound event patterns, each of which may be suggestive of a particular gastric motility dysfunction. For example, a gastric sound event rate of greater than four events per minute is typically seen in patients with tachygastria, which results in more rapid but relatively ineffective gastric function. An increased gastric sound event rate is also more likely to be present in patients having a mechanical gastric outlet obstruction. In contrast, bradygastria is a gastric motility dysfunction in which stomach peristaltic activity is slowed and which typically results in a decreased sound gastric event rate.

Additionally, another group of abnormal patients may have a broad gastric sound event rate distribution demonstrating a gastric sound event rate that is significantly different from the three events per minute rate that is predominant in healthy patients. Such a broad rate distribution is typically seen with diffuse gastric motor disorders that result in DGE.

Further, the gastric sound event propagation direction (ante or pro-peristaltic) and propagation speed may also be useful in diagnosing gastric motility dysfunctions such as DGE. Typically, normal patients have gastric sound events which propagate aborally (i.e., away from the mouth), while patients with DGE have gastric sound events which are antigrade and which typically propagate faster or slower than in healthy patients.

Still further, a gastric motility dysfunction is typically accompanied by an abnormal gastric sound event spectral content. For example, as gastroparesis (i.e., paralysis of the stomach) progresses, the stomach enlarges. The enlarged stomach cavity results in the generation of more lower frequency sounds, which may be detected using the technique described herein. Similarly, conditions such as spasmodic gastric wall changes due to electrolyte imbalances may lead to gastric sound events that have an abnormal spectral content.

Additionally, gastric electrical activity may be independently monitored (using, for example, electrogastrography or EGG) via surface electrodes. Such electrical activity may be used to test the coordination and timing between an EGG signal and gastric sound events. For example, the occurrence of gastric sound events at an abnormal timing may be indicative of an abnormal pathology.

What is claimed is:

1. A method of detecting a gastric motility dysfunction, comprising:
   acquiring a plurality of signals associated with sounds emanating from an abdominal region of a body;
   calculating an envelope of the plurality of signals;
   detecting a plurality of acoustic events based on the envelope of the plurality of signals;
   calculating a characteristic of the plurality of acoustic events; and
   determining whether the characteristic of the plurality of acoustic events corresponds to the gastric motility dysfunction.

2. The method of claim 1, wherein calculating the characteristic of the plurality of acoustic events includes determining locations within the abdominal region associated with the plurality of acoustic events.

3. The method of claim 2, wherein determining the locations within the abdominal region associated with the plurality of acoustic events includes using one of an arrival order, a signal attenuation, a relative time delay and a beam forming technique to determine the locations within the abdominal region.

4. The method of claim 1, wherein calculating the characteristic of the plurality of acoustic events includes calculating a dominant acoustic event rate associated with the plurality of acoustic events.

5. The method of claim 1, wherein calculating the characteristic of the plurality of acoustic events includes calculating an average acoustic event rate.

6. The method of claim 1, wherein calculating the characteristic of the plurality of acoustic events includes calculating one of a temporal characteristic and a spectral characteristic.

7. The method of claim 1, wherein determining whether the characteristic of the plurality of acoustic events corresponds to the gastric motility dysfunction includes determining whether the characteristic corresponds to delayed gastric emptying.

8. The method of claim 1, wherein determining whether the characteristic of the plurality of acoustic events corresponds to the gastric motility dysfunction includes comparing the characteristic associated with the plurality of acoustic events to a characteristic associated with a healthy condition.

9. The method of claim 8, wherein comparing the characteristic associated with the plurality of acoustic events to the characteristic associated with the healthy condition includes comparing the characteristic associated with the plurality of acoustic events to one of a predetermined spectral characteristic, a predetermined temporal characteristic and a predetermined location characteristic.

10. A system for detecting a gastric motility dysfunction, comprising:
an acoustic sensor adapted to sense sounds emanating from an abdominal region of a body;
a memory including software stored thereon; and
a processor coupled to the acoustic sensor and the memory and adapted to execute the software to:
acquire a plurality of signals associated with the sounds emanating from the abdominal region of the body;
calculate an envelope of the plurality of signals;
detect a plurality of acoustic events based on the envelope of the plurality of signals;
calculate a characteristic of the plurality of acoustic events; and
determine whether the characteristic of the plurality of acoustic events corresponds to the gastric motility dysfunction.

11. The system of claim 10, wherein the processor is further adapted to execute the software to calculate the characteristic of the plurality of acoustic events by determining locations within the abdominal region associated with the plurality of acoustic events.

12. The system of claim 11, wherein the processor is further adapted to execute the software to determine the locations within the abdominal region associated with the plurality of acoustic events by using one of an arrival order, a signal attenuation, a relative time delay and a beam forming technique.

13. The system of claim 10, wherein the processor is further adapted to execute the software to calculate the characteristic of the plurality of acoustic events by calculating a dominant acoustic event rate associated with the plurality of acoustic events.

14. The system of claim 10, wherein the processor is further adapted to execute the software to calculate the characteristic of the plurality of acoustic events by calculating an average acoustic event rate.

15. The system of claim 10, wherein the processor is further adapted to execute the software to calculate the characteristic of the plurality of acoustic events by calculating one of a temporal characteristic and a spectral characteristic.

16. The system of claim 10, wherein the processor is further adapted to execute the software to determine whether the characteristic of the plurality of acoustic events corresponds to the gastric motility dysfunction by determining whether the characteristic corresponds to delayed gastric emptying.

17. The system of claim 10, wherein the processor is further adapted to execute the software to determine whether the characteristic of the plurality of acoustic events corresponds to the gastric motility dysfunction by comparing the characteristic associated with the plurality of acoustic events to a characteristic associated with a healthy condition.

18. The system of claim 17, wherein the processor is further adapted to execute the software to compare the characteristic associated with the plurality of acoustic events to the characteristic associated with the healthy condition by comparing the characteristic associated with the plurality of acoustic events to one of a predetermined spectral characteristic, a predetermined temporal characteristic and a predetermined location characteristic.

19. The system of claim 10, wherein the acoustic sensor is one of an electronic stethoscope, an accelerometer, a contact microphone and a non-contact vibration sensor.

20. The system of claim 10, further including another acoustic sensor adapted to sense the sounds emanating from the abdominal region of the body.

21. The system of claim 10, further including one of a display and a printer coupled to the processor and adapted to indicate a diagnostic result associated with the gastric motility dysfunction.

22. A system for detecting a gastric motility dysfunction, comprising:
a computer readable medium; and software stored on the computer readable medium and adapted to be executed by a processor to:
acquire a plurality of signals associated with sounds emanating from an abdominal region of a body;
calculate an envelope of the plurality of signals;
detect a plurality of acoustic events based on the envelope of the plurality of signals;
calculate a characteristic of the plurality of acoustic events; and
determine whether the characteristic of the plurality of acoustic events corresponds to the gastric motility dysfunction.

23. The system of claim 22, wherein the software is further adapted to be executed by the processor to calculate the characteristic of the plurality of acoustic events by determining locations within the abdominal region associated with the plurality of acoustic events.

24. The system of claim 23, wherein the software is further adapted to be executed by the processor to determine the locations within the abdominal region associated with the plurality of acoustic events by using one of an arrival order, a signal attenuation, a relative time delay and a beam forming technique.

25. The system of claim 22, wherein the software is further adapted to be executed by the processor to calculate the characteristic of the plurality of acoustic events by calculating a dominant acoustic event rate associated with the plurality of acoustic events.

26. The system of claim 22, wherein the software is further adapted to be executed by the processor to calculate the characteristic of the plurality of acoustic events by calculating an average acoustic event rate.

27. The system of claim 22, wherein the software is further adapted to be executed by the processor to calculate the characteristic of the plurality of acoustic events by calculating one of a temporal characteristic and a spectral characteristic.

28. The system of claim 22, wherein the software is further adapted to be executed by the processor to determine whether the characteristic of the plurality of acoustic events corresponds to the gastric motility dysfunction by determining whether the characteristic corresponds to delayed gastric emptying.

29. The system of claim 22, wherein the software is further adapted to be executed by the processor to determine whether the characteristic of the plurality of acoustic events corresponds to the gastric motility dysfunction by comparing the characteristic associated with the plurality of acoustic events to a characteristic associated with a healthy condition.

30. The system of claim 29, wherein the software is further adapted to be executed by the processor to compare the characteristic associated with the plurality of acoustic events to the characteristic associated with the healthy condition by comparing the characteristic associated with the plurality of acoustic events to one of a predetermined spectral characteristic, a predetermined temporal characteristic and a predetermined location characteristic.

31. A method of detecting a gastric motility dysfunction, comprising:

acquiring acoustic event information associated with a body;

comparing the acquired acoustic event information to information associated with a healthy condition; and identifying the gastric motility dysfunction based on the comparison of the acquired acoustic event information to the information associated with the healthy condition.

32. The method of claim 31, wherein acquiring the acoustic event information associated with the body includes acquiring signals from a plurality of acoustic sensors associated with an abdominal region of the body.

33. The method of claim 31, wherein comparing the acquired acoustic event information to the information associated with the healthy condition includes comparing one of spectral information, temporal information and location information with the information associated with the healthy condition.

34. The method of claim 31, wherein comparing the acquired acoustic event information to the information associated with the healthy condition includes comparing an acoustic event rate to the information associated with the healthy condition.

35. The method of claim 31, wherein identifying the gastric motility dysfunction based on the comparison of the acquired acoustic event information to the information associated with the healthy condition includes identifying a delayed gastric emptying condition.

* * * * *